United States Patent
Katz et al.

(10) Patent No.: US 6,469,781 B1
(45) Date of Patent: Oct. 22, 2002

(54) PHOTOINDUCED NUCLEATION: A NOVEL TOOL FOR DETECTING MOLECULES IN AIR AT ULTRA-LOW CONCENTRATIONS

(75) Inventors: Joseph L. Katz, Baltimore, MD (US); Heikki Lihavainen, Masala (FI); Markus M. Rudek, Bruchkoebel (DE); Brian C. Salter, New Market, MD (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 197 days.

(21) Appl. No.: 09/629,468

(22) Filed: Aug. 1, 2000

(51) Int. Cl.[7] .................................. G01N 1/00
(52) U.S. Cl. .................. 356/37; 356/335; 356/336; 356/337
(58) Field of Search .................. 356/37, 335, 336, 356/337

(56) References Cited

U.S. PATENT DOCUMENTS

| | | | | |
|---|---|---|---|---|
| 4,734,451 A | * | 3/1988 | Smith | ................ 118/300 |
| 5,026,155 A | * | 6/1991 | Ockovic et al. | ............ 356/336 |
| 5,519,490 A | * | 5/1996 | Nakata et al. | ............... 356/246 |
| 5,872,622 A | * | 2/1999 | Schildmeyer et al. | ........ 356/339 |
| 5,903,338 A | * | 5/1999 | Mavliev et al. | ............. 356/338 |

* cited by examiner

Primary Examiner—Frank G. Font
Assistant Examiner—Roy M. Punnoose
(74) Attorney, Agent, or Firm—Bradley W. Smith; Mark P. Dvorscak; Paul A. Gottlieb

(57) ABSTRACT

A method and apparatus for determining the presence of molecules in a gas at concentrations of less than about 100 ppb. Light having wavelengths in the range from about 200 nm to about 350 nm is used to illuminate a flowing sample of the gas causing the molecules if present to form clusters. A mixture of the illuminated gas and a vapor is cooled until the vapor is supersaturated so that there is a small rate of homogeneous nucleation. The supersaturated vapor condenses on the clusters thus causing the clusters to grow to a size sufficient to be counted by light scattering and then the clusters are counted.

20 Claims, 7 Drawing Sheets

PHOTOINDUCED NUCLEATION: A NOVEL TOOL FOR DETECTING MOLECULES IN AIR AT ULTRA-LOW CONCENTRATIONS

The United States Government has rights in this invention pursuant to a Grant DE-FGO2-95ER62004 between the U.S. Department of Energy (DOE) and The John Hopkins University

BACKGROUND OF THE INVENTION

There are many substances which have very small vapor pressures, but whose presence in air is nonetheless undesirable because they are very toxic or indicate the presence of unwanted substances such as explosives, drugs, etc. Consider the explosives 2,4,6-trinitrotoluene (TNT), 2,4-dinitrotoluene (2,4-DNT), and 2,6-dinitrotoluene (2,6-DNT). The saturation concentrations of these substances in air at room temperature are approximately 10 ppb, 300 ppb, and 700 ppb, respectively, numbers large enough to suggest that 2,4- and 2,6-DNT can be detected using existing techniques. However, in the real world, a terrorist is unlikely to present the detector with a volume of saturated air. At best, the fraction of molecules available to a 'sniffer' will be further reduced by a few orders of magnitude. Therefore, detectors must be able to detect these explosives at vapor concentrations a few orders of magnitude less than their saturation concentrations.

We here disclose the development of a novel detection method using photoinduced nucleation and the demonstration of its ability to detect and quantify TNT, 2,4-DNT, and 2,6-DNT in humid air at concentrations as small as 5 parts per trillion (ppt), 10 ppt, and 10 ppt, respectively. Thus Photo Induced Nucleation Detection (PIND) can be used to detect these explosives, even if their concentration at the detector is 2000, 30000, and 70000 fold smaller than their saturation concentrations.

The phenomenon that upon irradiation (illumination) with light of suitable wavelength and intensity, certain organic compounds (e.g., o-tolualdehyde) (OTA) cause very efficient nucleation of supersaturated vapors has been previously reported. This phenomenon (which was named photoinduced nucleation) could be utilized to detect and identify substances, even when they are present in very low concentrations. However, the experimental device then used was not designed to sample substances in air. The substances to be detected were placed in a liquid pool from which molecules evaporated to give a known vapor concentration. The substances could not be introduced from outside of the device since molecules from a vapor injection would diffuse to the liquid pool, resulting in sample losses and contamination of the pool. Also, in the above-mentioned work, the photoinduced nucleation occurred by illuminating (with UV light) the substance being detected when it was in a supersaturated vapor. Therefore, it was unknown whether the presence of a vapor which was supersaturated played an essential role in the photoinduced nucleation process.

SUMMARY OF THE INVENTION

It is an object of the invention to provide a method and apparatus to detect molecules of substances in the air at extremely low concentrations of less than about 100 ppb.

Another object of the invention is to provide a method and apparatus to detect molecules of substances such as pollutants and explosives in concentrations of a few ppt.

Still another object of the invention is to provide a method and portable apparatus for using supersaturated vapors to increase the size of photoproducts produced by exposing air containing detectable substances to light to produce photo excited molecules.

A still further object of the invention is to identify the presence, density and concentration of detectable substances at very low concentrations.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

The present invention together with the above and other objects and advantages may best be understood from the following detailed description of the embodiment of the invention illustrated in the drawings, wherein.

DETAILED DESCRIPTION OF THE INVENTION

PIND consists of illuminating an air stream containing molecules of the substance to be detected with UV light as it flows through 10 cm a fused silica cell. It should be understood that there are various devices for illuminating flowing air, but the fused silica cell is used by way of example. Seconds later this stream, which now contains photoproducts produced inside the fused silica cell, flows into the location where it mixes with a stream that is saturated with nucleating vapor (i.e., into an Ultrafine Condensation Particle Counter, TSI model 3025A ). The combined stream is then cooled to make the vapor supersaturated. Note that the molecules are in a non-supersaturated environment when they are illuminated with UV light. This shows that a supersaturated vapor is not needed to form or stabilize the photoproducts. Its only essential role is to nucleate onto the photoproducts thereby causing their growth (by condensation) into particles whose sizes are large enough to be readily detectable by light scattering.

The OTA was obtained from Aldrich at a stated purity of 97%. The 2,4- and 2,6-DNT were obtained from Aldrich with a stated purity of 97–98%. TNT was obtained from Supelco in vials that were reported to contain one mg of TNT dissolved in one $cm^3$ of acetonitrile. Ultra Zero Grade air was obtained from Airgas (Linthicum, Md.) with a reported total hydrocarbon concentration less than 0.1 ppm. The air was further purified by flowing through an activated carbon filter. This filter was placed in a dry ice bath, and the incoming air was precooled by flowing through five feet of corrugated Teflon® tubing which also was in the dry ice bath.

Figure 1:
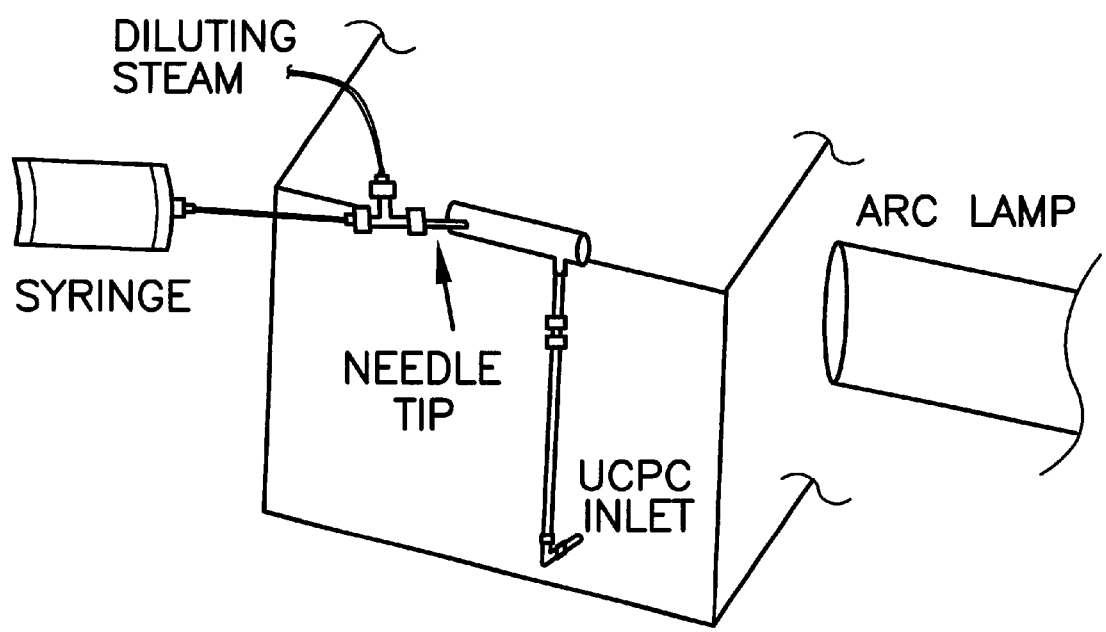
FIG. 1 is a schematic representation of experimental setup used to produce a known test concentration of the composition having very low vapor pressures.

Producing a vapor of known concentration in the parts per trillion range is not simple. One way of doing so is to flow clean air over crystals of the substance to be detected for a time sufficiently long that its concentration in the air reaches its saturation concentration using the apparatus illustrated in FIG. 1. A procedure which produces a saturated stream consists of using a 150 mm long, 0.8 mm I.D. needle which is coated on its inside with the substance to be detected. Then this saturated stream is diluted by mixing with a much larger air stream to give the desired vapor concentration. The concentration of the test stream is the concentration of the needle stream times the dilution ratio (i.e., the ratio of flow through the needle to the total flow). However, the supposedly known test concentration will be inaccurate if the needle stream is not saturated or if molecules in the test stream subsequently adsorb onto any surfaces.

The inside of the needle is coated by making a concentrated solution of the substance using a volatile solvent and drawing this solution into a needle. The solution then is allowed to drain out of the needle, leaving some solvent (with dissolved substance molecules) on the needle walls. Since the equilibrium vapor pressure of the solvent is typically four to five orders of magnitude greater than that of the substance to be detected, the solvent preferentially evaporates and diffuses out of the needle, leaving behind only the substance. After several hours, clean air is blown through the needle to remove the last traces of solvent. Those substance molecules which are deposited in the last centimeter of the inside of the needle are then removed by heating the end of the needle, while keeping the rest of the needle cool by clamping it in a vise. This cleaning was done to prevent diffusion of the substance out of the needle (which would result in a higher concentration than calculated based on the dilution ratio). The outside of the needle is then wiped repeatedly with Kimwipes® (very slightly wet with ethanol) to remove any of the substance which may have adsorbed onto it.

To verify that the length of the coated needle was sufficient to obtain a saturated stream in the concentration range and at the flow rates that were used in the studies reported here, two needle lengths (150 mm and 75 mm) were compared. Both produced exactly the same nucleation rates (at the same flow rates).

The Ultrafine Condensation Particle Counter (UCPC) worked best at a total flow rate of 18,000 $cm^3$/hr. Thus, a TNT stream whose concentration is 5 ppt was produced by setting the flow rate through the needle 10 $cm^3$/hr because the equilibrium vapor pressure of TNT at 25° C. is reported to be 10 ppb[1] (i.e., 10 ppb×10/18,000=5 ppt). The needle temperature was kept at room temperature by flowing room temperature air over the needle.

The flow rate through the coated needle is controlled by a syringe pump (KD Scientific 100 Automatic Syringe Pump), which pushes the piston of a 50 $cm^3$ gas tight syringe (Hamilton #1050). The needle is sealed with a Teflon® ferrule to a Swagelock® female connector, which itself is attached to a stainless steel tee. The diluting stream (18,000 $cm^3$/hr) enters at the tee and flows alongside the needle for about 3 cm in the same direction of the air flowing inside the needle. This flow alongside the needle prevents backflow and back diffusion of the gas exiting the needle; thus adsorption of the substance onto the outside of the needle or the connector walls is eliminated. The combined stream flows into a 100 mm long, 20 mm i.d. UV-transparent fused silica cell (Fisher 280 QS 10000) where it is illuminated. Electrical heating tape is used to heat the cell to minimize adsorption of the substance onto its wall. The flowing stream then is cooled to room temperature before it enters the UCPC.

The cell is irradiated with light from a 100-Watt arc Mercury lamp. Generally, light having wavelengths in the 200 nm to about 350 nm is acceptable with both monochromatic light sources or tunable light sources being satisfactory. For instance, white light or lasers are acceptable sources. To determine the nucleation rate dependence on light intensity, various combinations of perforated steel plates were placed between the lamp and cell. The dependence of the nucleation rate on wavelength was determined by using a monochromator illuminated by a 150-Watt Xenon arc lamp.

The flowing stream (containing the photoproducts formed in the cell) flows into the UCPC Here it becomes saturated with n-butanol and then is cooled to make it supersaturated. It should be understood that the supersaturated vapor can be water vapor or an organic including mixtures, such as an alcohol, alkane, or an aromatic. Condensation of butanol occurs on those photoproducts which are large enough to serve as condensation nuclei, causing them to grow into micron sized droplets which then are counted by the optical detector using light scattering. Note that the supersaturation being produced with this flow chamber is not accurately known. In principle, supersaturation and temperature profiles can be calculated, but because of the many uncertainties this was not meaningful. The measurables which are known are the temperature of the saturator (TS) and the temperature of the condenser (TC).

There is a supersaturation that will maximize detection sensitivity. Increasing the supersaturation decreases the minimum detectable photoproduct size and thus does increase the measured nucleation rate. However, increasing the supersaturation also increases even more strongly the background nucleation rate (i.e., the nucleation which occurs when the flowing air stream does not contain molecules of the substance being detected). This background rate results from homogeneous nucleation of the supersaturated vapor, ion induced nucleation, and binary homogeneous nucleation of water with the supersaturated vapor (when water vapor is present). Also, too small a supersaturation is not optimal since the rate of data acquisition becomes too small, and the background does not decrease to zero. For these experiments with air, the greatest sensitivity was obtained by using a supersaturation (TS=39, TC=7) that caused a background counter reading of about 10 droplets per $cm^3$.

What is actually being measured by PIND is the droplet concentration, i.e., the number of droplets counted per unit of time divided by the volumetric flow rate. However, the term "droplet concentration" can cause confusion because nucleation processes typically are quantified by "nucleation rate" and "concentration" is being used in this application for the concentration of the molecules of the substance being detected in the incoming air stream. To avoid confusing these two uses of the word "concentration", the "droplet concentration" (i.e., the photoinduced droplet concentration minus the background droplet concentration) will be referred to as the nucleation rate.

Adsorption of the molecules to be detected in the sample stream onto any surfaces (e.g., tubing, the fused silica cell, and Swagelok® connectors) will give misleading results. Initially adsorption will decrease the apparent substance concentration; after flowing for some time (e.g., several hours) steady state may be reached. However, if one does not wait until steady state and decreases the test sample concentration or even turns it off, the substance will continue being detected because it is desorbing from the surfaces. Thus, it may appear that this lower test concentration has been detected, that the background rate is much higher, or that there is a very long decay time. To minimize adsorption, the area of stainless steel exposed to the test concentration was minimized. Also, the fused silica cell was heated to decrease the amount of adsorbed substance. It is known that retention of TNT vapor by quartz and stainless steel was undetectable when these materials were heated to 100–120° C., and 150° C., respectively.

Figure 2:
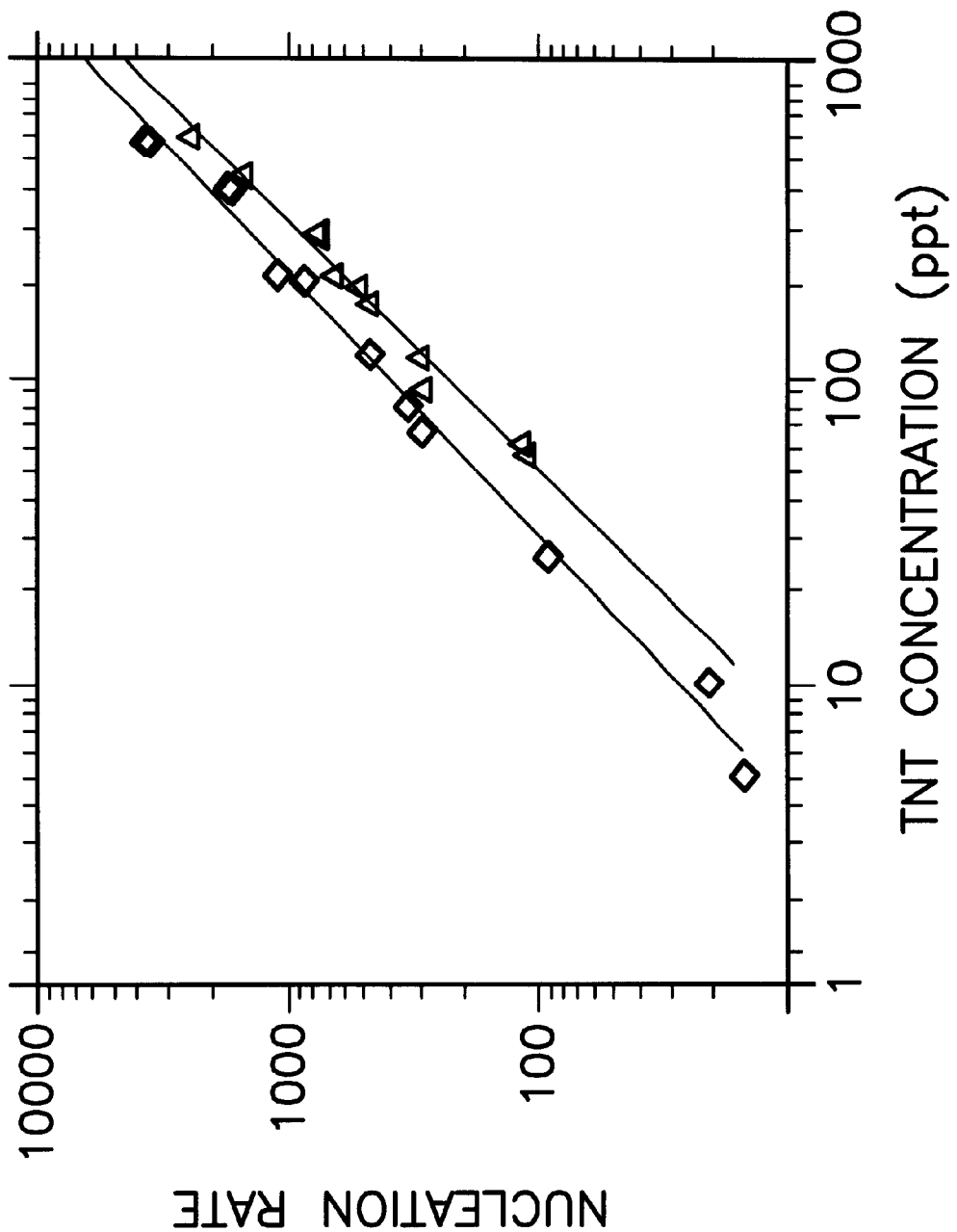
FIG. 2 is a graphical representation of the relationship between the nucleation rate dependence on TNT concentration in dry and humid air with a relative light intensity (white light) of 1 at optimum supersaturation.

As can be seen from FIG. 2, the lowest clearly detected concentration of TNT in humid air was 5 ppt. For 2,4-DNT and 2,6-DNT lowest detection limits at humid air were 10 ppt for both substances. Note that all the results were obtained without the use of any preconcentration technique.

Previous non-flow studies showed that the measured photoinduced nucleation rates are described by power laws, i.e., $$J[C]^a[I]^b$$

where J is the nucleation rate, [I] is the light intensity, [C] is the concentration of the light-absorbing substance, and a and b are constants.

Figure 3:
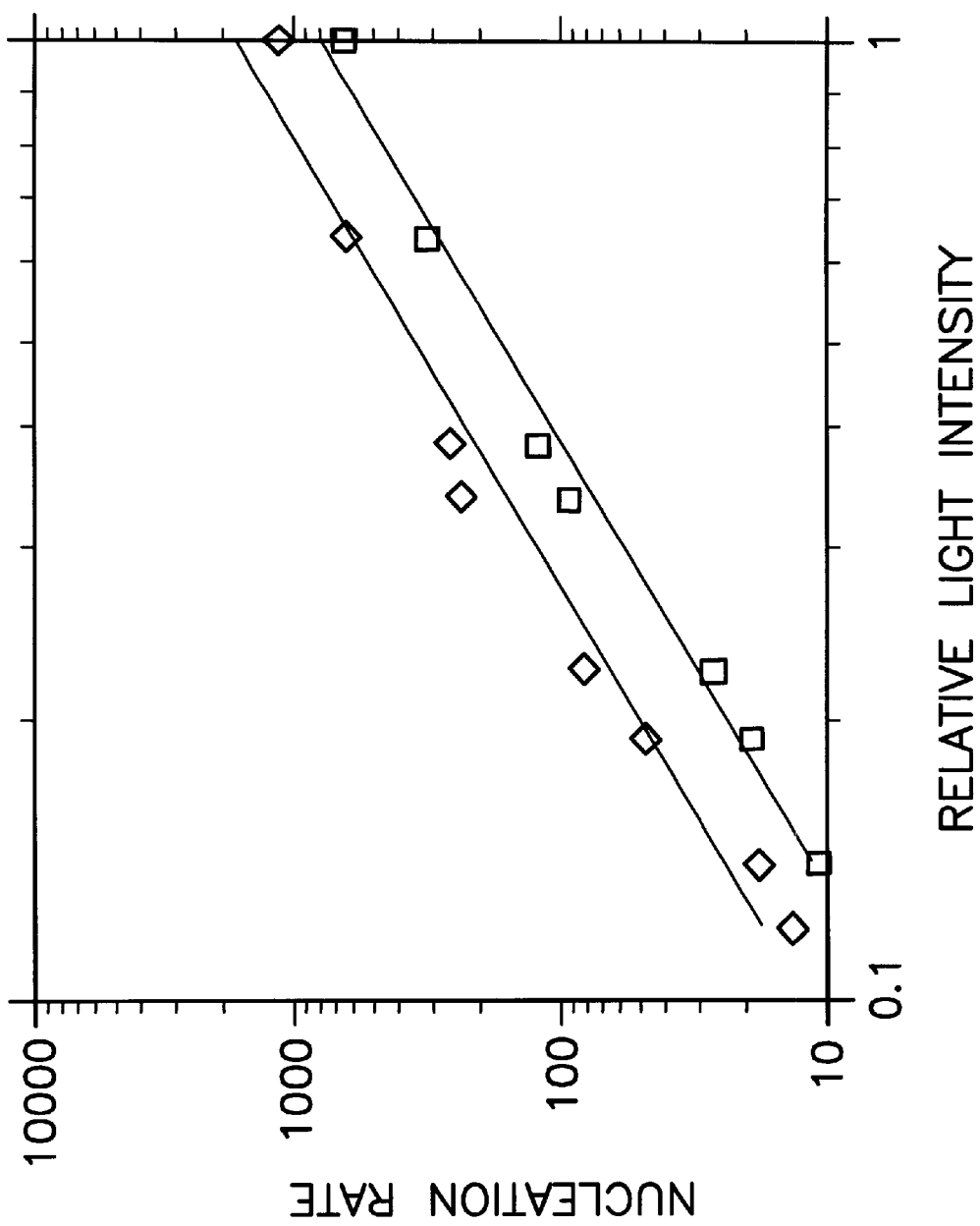
FIG. 3 is a graphical representation of the nucleation rate dependence on light intensity (with white light) for TNT at 200 ppt in dry and humid air at optimum saturation (the data points for dry air were corrected to 200 ppt from 900 ppt using the power law)

As can be seen in FIGS. 2 and 3, the nucleation rate for PIND also is described by power laws. Furthermore, b is about 2.2 and a is about 1.2 for TNT in both dry and humid air (see FIGS. 2 and 3). Thus, the TNT concentration needed to obtain some detectable nucleation rate decreases as $[I]^{-2.2/1.2}$. Therefore, if this power law holds for higher light intensities, a ten fold increase in light intensity will result in about a seventy fold decrease in detectable concentration. If a 1000-Watt lamp were to have been used instead of a 100-Watt lamp (in a lamp housing with the same light collection efficiency), the detection limit for TNT would have decreased from 5 ppt to about 0.07 ppt. Measurements were also done using helium or nitrogen as a carrier gas. They showed similar power law behavior as air as a carrier gas.

Since ambient air normally has some water vapor in it, measurements also were made with TNT both in dry air and in air at 30% relative humidity. Doing so increased the nucleation rate about two fold (see FIG. 2). Note that the presence of water does not change the concentration and intensity power laws. Measurements also were made which showed that this rate enhancement is not due to photoinduced nucleation of water. However, the addition of a water vapor stream did cause a photoeffect due to trace levels of contamination in the water, but this background photoeffect with water was accounted for when determining the water enhancement.

Figure 4:
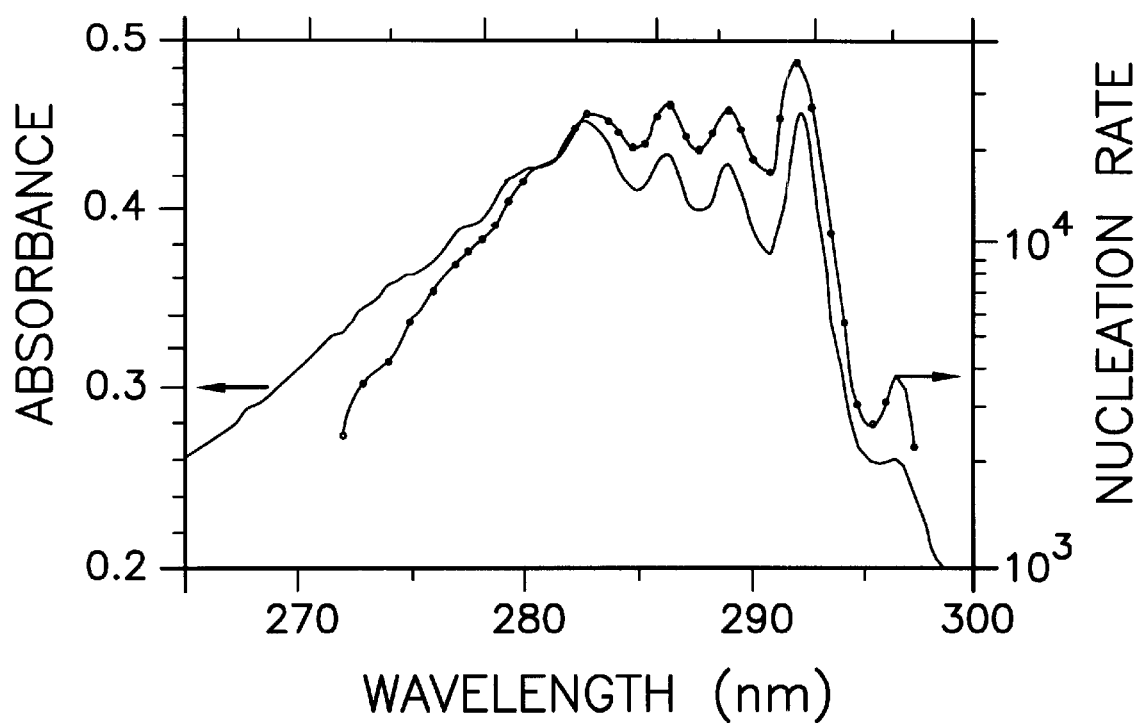
FIG. 4 is a graphical representation of the nucleation rate dependence on wave length (IE), the nucleation rate spectrum (for OTA in air and the vapor phase UV spectrum of OTA), the OTA nucleation rate spectrum being measured with 100 ppm of OTA in a flowing air stream using a 150 W XE lamp in a monochromator.
Figure 5:
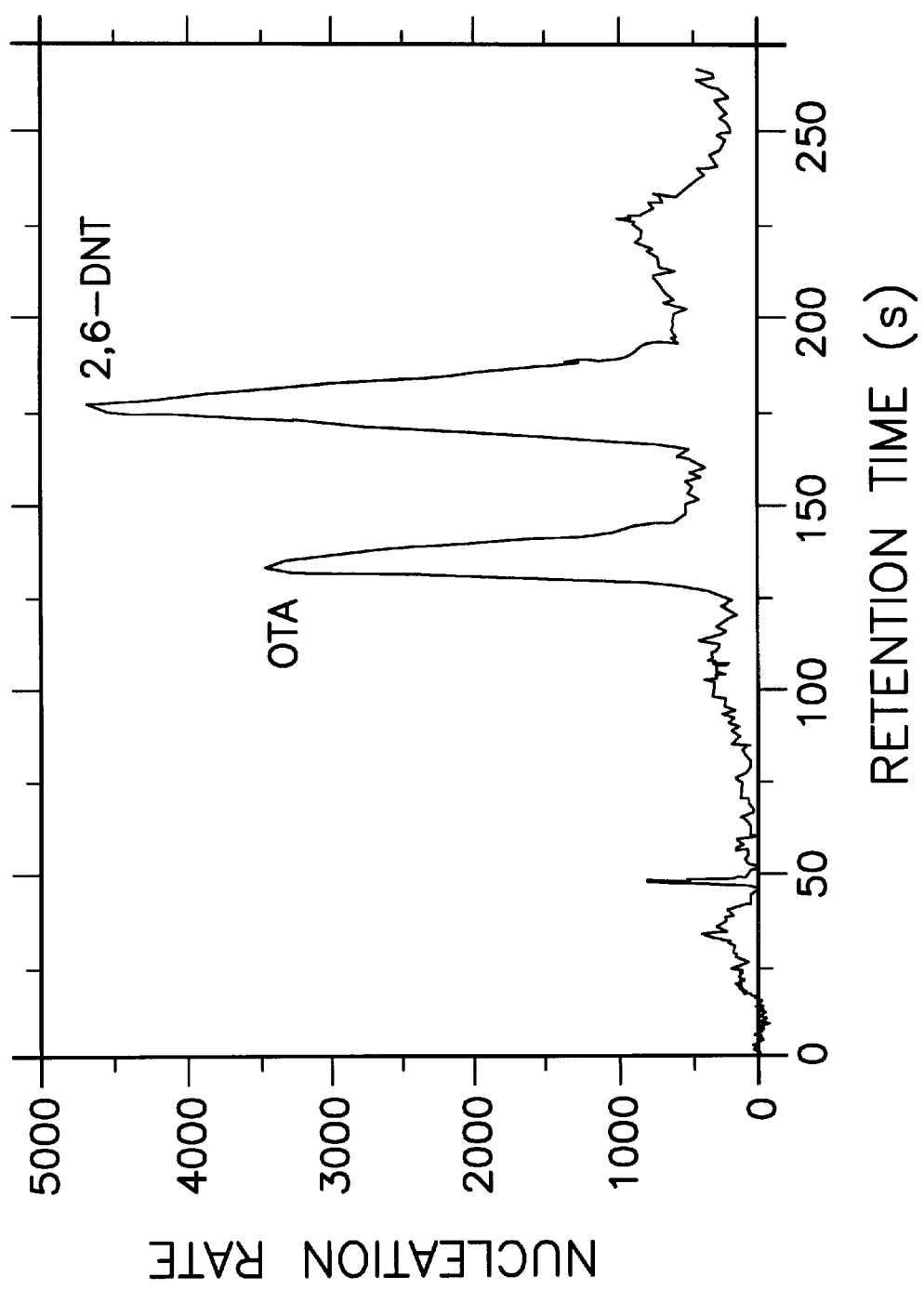
FIG. 5 is a graphical representation of the relationship between nucleation rate and retention time for OTA and 2,6-DNT by calibration using a gas chromatograph using the photoinduced nucleation detection.
Figure 6:
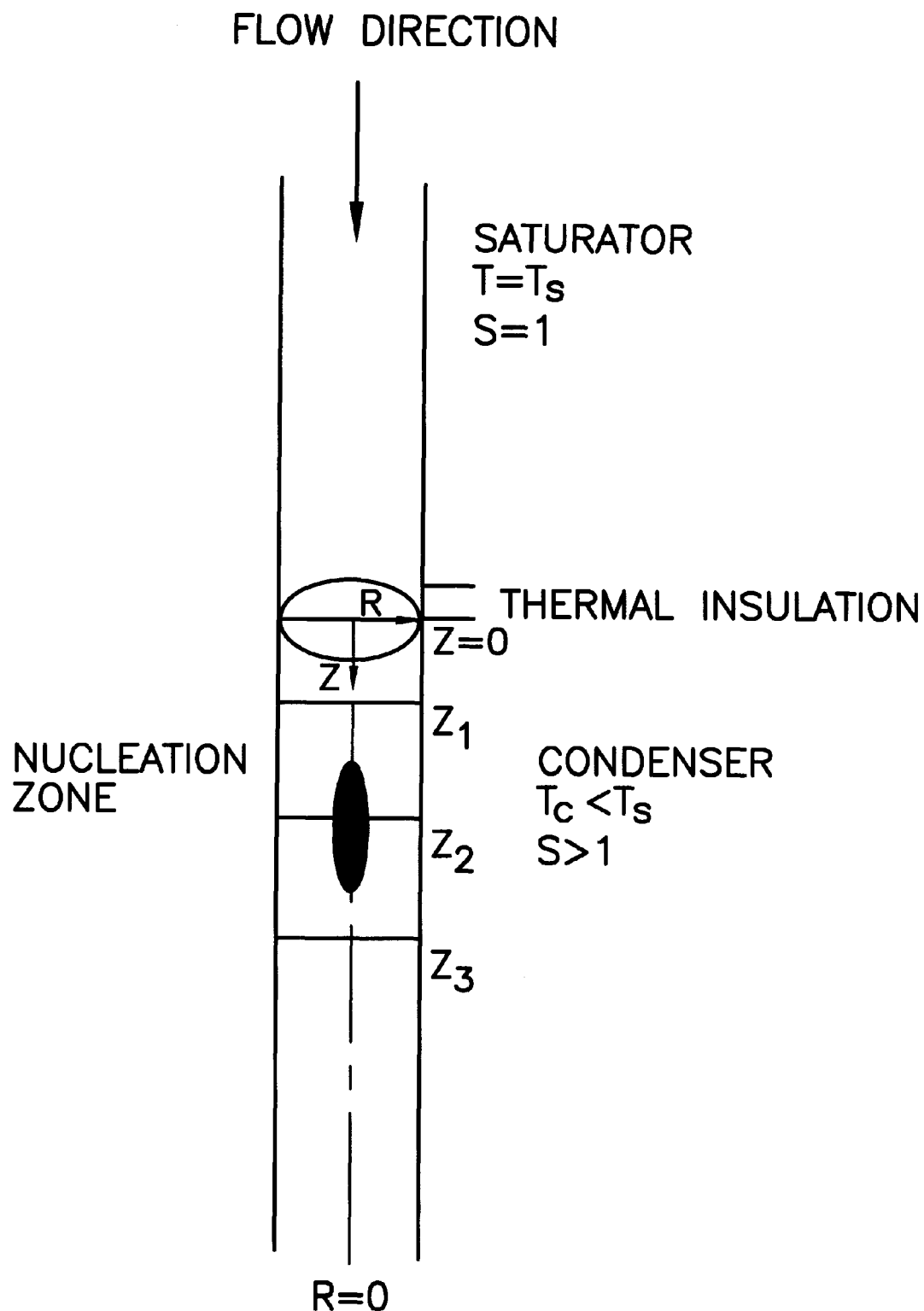
FIG. 6 is a graphical representation of a laminar flow diffusion chamber.

In addition to detecting, it is important to identify the substance causing the photoinduced nucleation. One way of accomplishing this is by measuring the dependence of the nucleation rate on the wavelength of the UV light. Note that the wavelength region can include light in the UV or visible region if molecules of the substance absorb light at that wavelength. FIG. 4 shows the nucleation rate dependence on wavelength (called "the nucleation rate spectrum") for a flowing stream of air containing 100 ppm of OTA illuminated by light from a 150 W Xenon arc lamp-monochromator combination. Also shown is its vapor phase light absorption spectrum. One sees that the light absorption spectrum exactly matches the variation with wavelength of the nucleation rate spectrum. Thus, the nucleation rate spectrum enables one to identify the substance. One also can determine the concentration by calibration.

A comparison similar to FIG. 4 was not made for TNT, 2,4-DNT, or 2,6-DNT because their vapor phase concentrations (at ambient temperatures) are so minuscule that their vapor phase light absorption spectra are much too weak to be measurable. Measurements of their nucleation rate spectra were not made since our arc lamp-monochromator combination produces light intensities which are about 10 to 500 fold too weak, even if their concentrations are at the maximum possible, i.e., their saturation concentrations.

Another means of obtaining specificity is using PIND as the detector of a gas chromatograph(GC). GC/PIND studies were made which prove the feasibility of injecting a 10 $cm^3$ gas sample, consisting of very low concentrations of two substances in air, into the GC and then, using white light, detecting each individually. FIG. 5 shows the results obtained when a gas sample, consisting of air and the vapors of two substances, 2,6-DNT (at a concentration of 4 ppb) and OTA were injected into a GC. Note that this figure enables one to both identify the individual substances and their concentrations. This is done by comparing their retention times (the time from injection until the peak nucleation rate ) and the values of the areas under the peaks with those obtained under identical operating conditions, one substance in air at a time.

The diffusion cloud chamber works very well for many situations. However, using them to sample a gas stream, either an ambient air sample or from a gas chromatography, causes difficulties. Introduction of a gaseous sample upsets the steady-state operation. By the time the transients have disappeared, significant and uncontrolled nucleation may have occurred. The substance causing the nucleation will end up in the liquid pool and its concentration, by the time stable operation is possible, will be very uncertain. With a flow version of the diffusion cloud chamber we were able to circumvent these problems.

The laminar flow diffusion cloud chamber working principle is very similar to a diffusion cloud chamber, see FIG. 6. First the flow of carrier gas is saturated with vapor in the saturator. We used helium and nitrogen as carrier gas, by way of example only. After the saturator, the flow enters the condenser. The condenser is maintained at a lower temperature than the saturator and these two parts are thermally separated. The laminar flow in the condenser is cooled by heat exchange with the condenser wall. The cooling results in high saturations with the maximum at some distance away from the condenser inlet on the centerline. The supersaturation can be adjusted by changing the temperature difference between saturator and condenser. The temperature and vapor concentration profiles inside the condenser can be calculated by solving the steady-state equation for molecular diffusion and thermal conductivity. The sample flow is introduced to the main flow just before the inlet of the condenser part. The construction of the end of the sample tube makes sure that flows are well mixed. The beginning of condenser tube is illuminated with the UV light with suitable wavelength and intensity.

Several characteristics of any measurement technique must be evaluated to determine its appropriateness for use in the monitoring chemical contaminants. Among the more important characteristics are sensitivity, selectivity portability, cost and complexity. Sensitivity and selectivity are often particularly demanding parameters. Portability is often high priority item. Likewise, cost may be quite important when deciding on a measurement technique, particularly in large surveys. A final point for consideration is the complexity of the technique and the degree of skill and training required to obtain quality results.

An instrument that has a different set of strengths will be especially valuable to detect and monitor chemical contaminants. Following are advantages of using photoinduced nucleation in the laminar flow diffusion cloud chamber (hereafter referred to as flow chamber) for this purpose. Photoinduced nucleation in the flow chamber is capable of a reasonably fast response (better than 10 sec.), so the user can immediately take advantage of the information gained such as monitoring relatively short-lived species.

Furthermore, in initial studies using the flow chamber, substances which are typical of those causing concern in subsurface environments, e.g., acetone, benzylamine and toluene, have been detected by sub-ppm concentrations. Thus, photoinduced nucleation in the flow chamber is as sensitive as other currently available detection techniques and in many case may be one, two, or even more orders of magnitude more sensitive, and will be of great value for detecting species that otherwise are not determined.

Figure 7:
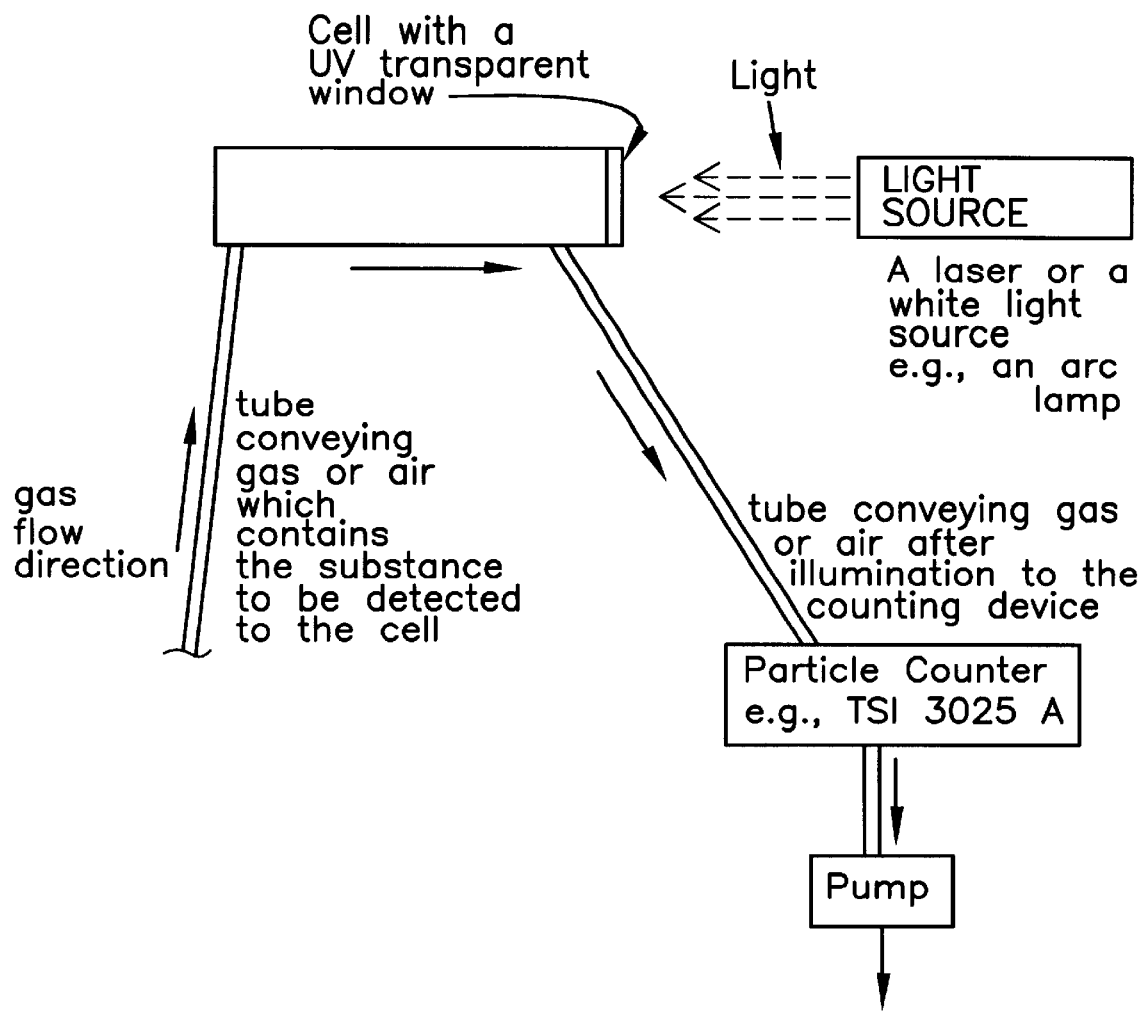
FIG. 7 is a schematic representation of a portable apparatus for practicing the invention.

Referring now to FIG. 7, there is disclosed a schematic representation of an apparatus which may be portable for practicing the invention. As shown, there is an inlet to conveying gas or air which contains the substance to be detected which leads to a cell with a UV transparent window shown in the schematic representation at one end thereof. A light source such as a laser or a white light source, for instance an arc lamp, emits light to and through the UV transparent window in the cell. Gas within the cell irradiated or illuminated and photoproducts occur. The gas with the photoproducts thereafter leave the cell falling down the tube which connects the cell to a particle counter, such as a TSI model 3025A. A pump may be provided within the particle counter or separate to establish the gas or air flow. In those situations where the incoming gas or air flow is under pressure higher than atmospheric pressure, there may be no need for a pump in combination or in addition to the particle counter to draw air or gas through the system.

Instruments of different types have been developed for real-time or quasi-real-time time detective of chemical contaminants in air. Most have been developed for industrial hygiene and ambient environment air applications. There are portable mass spectrometers (MS), derivative UV absorption spectrometers (DUVAS), infrared (IR) spectrometers, and high pressure liquid chromatographs (HPLC). Other monitoring instruments, based upon principles of atmospheric pressure chemical ionization (APCI) of analyte, include continuous, flow through electron capture detectors (ECD), and ion mobility spectrometers (IMS). Field portable gas chromatographs (GC) with photoionization (PI), thermal conductivity (TC), and/or flame ionization detectors are also available. These instruments can be capable of a real-time or near real time response and can have limits of detection at part per billion levels. However, they have limitations. Mass spectrometers are relatively costly and require experienced personnel. DUVAS, IR, and IMS are portable, but having limited selectivity. Gas chromatography in conjunction with different detectors, e.g., MS, ECD, PID, and FID, is a powerful detection technique, but cost and complexity restrict application.

Although photoinduced nucleation in the flow chamber can be a particularly powerful tool when used as a stand-alone monitor, it can be even more powerful when linked to a gas chromatography. The phenomena that cause retention by the GC column packings are not the same as the phenomena that cause UV-absorption (and hence photoinduced nucleation). Photonucleation in the flow chamber is able to discriminate among species that a GC may have difficulty separating, e.g., discrimination between ortho-, meta-, and para-xylene. Thus, a laminar flow diffusion cloud chamber, used in conjunction with GC (or other separation technique), provides significantly improved detection selectivity and species identification capability.

A novel tool for the detection and identification of substances in air at ultra-low concentrations has been developed. This tool, photoinduced nucleation, not only is extremely sensitive, but also has substance specificity due to the dependence of the nucleation rate on illumination wavelength PIND, when used with tunable UV light to monitor air, can accurately identify and quantify the concentration of the substances based on their nucleation rate spectrum. Alternatively, PIND can be used with white light in conjunction with a GC to sample air and identify the substances. Photoinduced nucleation has been reported with a variety of substances, including o-tolualdehyde, p-tolualdehyde, crotonaldehyde, benzoic acid, o-nitrotoluene, $CS_2$, $SO_2$, $Cl_2$, mercury, DNT, and TNT. Therefore, PIND may have many applications, including room air monitoring, factory floor monitoring, pollutant detection, and narcotics detection. The figures disclosed herein show that PIND detects TNT at concentrations as small as a few parts per trillion in ambient air, suggesting that this technology will be useful for explosives detection.

While there has been disclosed what is considered to be the preferred embodiment of the present intention, it is understood that various changes in the details may be made without departing from the spirit, or sacrificing any of the advantages of the present invention.

The embodiments of the invention in which an exclusive property or privilege is claimed are defined as follows:

1. A method of determining the presence of molecules in a gas at concentrations of less than about 100 ppb, comprising providing light having wavelengths in the range from about 200 nm to about 350 nm; illuminating a flowing sample of the gas with the light causing the molecules if present to form clusters, forming a mixture of the illuminated gas and a vapor, cooling the mixture until the vapor is supersaturated so that there is a small rate of homogeneous nucleation, the supersaturated vapor condensing on the clusters thus causing the clusters to grow to a size sufficient to be counted by light scattering, and counting the clusters.

2. The method of claim 1, wherein the light is white light.

3. The method of claim 1, wherein the light source is from a laser.

4. The method of claim 1, wherein the gas flows through a cell with a UV-transparent window through which it is illuminated by the light to form photoproducts.

5. The method of claim 4, wherein the vapor is water vapor or an organic.

6. The method of claim 4, wherein the vapor is selected from water vapor, an alcohol, an alkane or an aromatic.

7. The method of claim 1, wherein the light source is tunable.

8. The method of claim 1, wherein the molecule the presence of which is determined is one or more of a trinitrotoluene, a dinitrotroluene, and a tolualdehyde.

9. A method of determining the presence and identity of molecules in a gas at concentrations of less than about 100 ppb, comprising providing light having wavelengths in the range from about 200 nm to about 350 nm; illuminating a flowing sample of the gas with the light causing the molecules if present to form clusters, forming a mixture of the illuminated gas and a vapor, cooling the mixture until the vapor is supersaturated so that there is a small rate of homogeneous nucleation, the supersaturated vapor condensing on the clusters thus causing the clusters to grow to a size sufficient to be counted by light scattering, counting the clusters, determining the dependence of the number of clusters counted per unit time on the wavelength of the illuminating light, and comparing the determined dependence to known gas phase UV light absorption spectra or to the measured dependencies of known molecules.

10. The method of claim 9, wherein more than one molecule is determined and identified.

11. The method of claim 9, wherein the molecule is one or more of a trinitrololuene, a dinitrotoluene and a tolualdehyde.

12. A method of determining the presence and identity and concentration of a molecule in a gas at concentrations of less than about 100 ppb, comprising providing light having wavelengths in the range from about 200 nm to about 350 nm; illuminating a flowing sample of the gas with the light causing the molecules if present to form clusters, forming a mixture of the illuminated gas and a vapor, cooling the mixture until the vapor is supersaturated so that there is a small rate of homogeneous nucleation, the supersaturated vapor condensing on the clusters thus causing the clusters to grow to a size sufficient to be counted by light scattering, counting the clusters, determining the dependence of the number of clusters counted per unit of time on the wavelength of the illuminating light, comparing the determined dependence to known gas phase UV light absorption spectra or to the measured dependencies of known molecules, and comparing the number of clusters counted per unit of time of the molecule to a known reference of counts per unit of time produced by known concentrations of the identified molecule to identify the concentration of the identified molecule.

13. The method of claim 12, wherein the molecule concentration is in parts per trillion.

14. The method of claim 12, wherein the molecule includes more than one compound and further comprising separating the compounds for identification by gas chromatograph or by selectively limiting the wave lengths of the illuminating light to nucleate a specific compound or molecule.

15. Apparatus for determining the presence of a molecule in a gas at concentrations of less than about 100 ppb, comprising a light source providing light having wavelengths in the range from about 200 nm to about 350 nm; a chamber containing a flowing sample of the gas illuminated by the light causing the molecules if present to form clusters, mechanism forming a mixture of the illuminated gas and a vapor, mechanism for supersaturating the vapor so that there is a small rate of homogeneous nucleation, the supersaturated vapor condensing on the clusters thus causing the clusters to grow to a size sufficient to be counted by light scattering, and mechanism for counting the clusters.

16. The apparatus of claim 15, and further comprising mechanism for determining the dependence of the number of clusters counted per unit of time on the wavelength of the illuminating light, and mechanism comparing the determined dependence to known gas phase UV light absorption spectra or to the measured dependence of known molecules.

17. The apparatus of claim 16, and further comprising mechanism for comparing the number of clusters counted per unit of time of the molecule to a known reference of counts per unit of time produced by known concentrations of the identified molecule to identify the concentration of the identified molecule.

18. The apparatus of claim 15, wherein the mechanism forming a mixture of the illuminated gas and a vapor is a laminar flow diffusion cloud chamber.

19. The apparatus of claim 15, wherein the light source is a tunable laser.

20. The apparatus of claim 15, wherein the light source emits white light.

* * * * *